United States Patent [19]

Sampson et al.

[11] Patent Number: 5,085,849

[45] Date of Patent: Feb. 4, 1992

[54] D-LIMONENE CONTAINING SPACE OR ROOM AEROSOL DEODORANT

[75] Inventors: Dennis Sampson, Maplewood; Robert M. Smith, Ballwin, both of Mo.

[73] Assignee: Par-Way Group, Costa Mesa, Calif.

[21] Appl. No.: 556,361

[22] Filed: Jul. 20, 1990

[51] Int. Cl.$^5$ ............................................. A61L 9/04
[52] U.S. Cl. .................................... 424/45; 424/76.4; 424/76.6
[58] Field of Search .................. 424/76.6, 76.4, 83, 424/78, 45

[56] References Cited

U.S. PATENT DOCUMENTS

| | | | |
|---|---|---|---|
| 3,198,251 | 8/1965 | Shore | 424/76.6 |
| 3,954,964 | 5/1976 | Kuderna | 424/76.4 |
| 4,362,841 | 12/1982 | Minatono | 424/83 |
| 4,891,216 | 1/1990 | Kross | 424/78 |
| 4,923,977 | 8/1990 | Lang | 424/45 |

Primary Examiner—Thurman K. Page
Assistant Examiner—William E. Benston, Jr.
Attorney, Agent, or Firm—James A. Quinton; Frank Frisenda, Jr.

[57] ABSTRACT

A deodorizing terpene preferably a citrus oil distillate containing substantial amounts of d-Limonene is emulsified with polyethylene glycol nonylphenyl ether to form an oil phase. The resulting oil phase is added to a water phase having a pH of from 8.5 to 10 to form a water-in-oil emulsion having a viscosity under 500 cps preferably about 100 cps. The resulting emulsion is then used as the deodorizing concentrate for filling the aerosol cans. A propellant, preferably an alkane propellant is then added to the cans in an amount of 25-40% of the concentrate. The product is then held for 12 to 24 hours at room temperature during which time it forms a non-flammable, stable oil-in-water, emulsion which can be used as a highly effective aerosol space or room deodorant.

16 Claims, No Drawings

D-LIMONENE CONTAINING SPACE OR ROOM AEROSOL DEODORANT

BACKGROUND OF THE INVENTION

1. Field of the Invention

The subject invention relates to aerosol space or room deodorants. In particular the invention relates to a d-Limonene containing aerosol space deodorant.

2. Prior Art

Naturally occurring terpenes are derived from citrus oils. The primary active ingredient in such oils limonene. D-Limonene is used in the prior art as an aerosol space or room deodorant. However, most common aerosol space deodorants contain over 50% by weight of propellant, alcohols, or isoparaffinic hydrocarbons or even aliphatic hydrocarbons to form stable or unstable emulsions to effect adequate dispersions of active ingredients. In addition, other environmental questionable additives and propellants such as chlorofluoro hydrocarbons have been used. For example, German Patent No. 1,812,440 shows a limonene composition containing carbon tetrachloride and chlorofluorohydrocarbon propellant.

D-Limonene has been mixed with surfactants and other additives in order to form useful d-Limonene products. U.S. Pat. No. 4,533,487 discloses a d-Limonene containing product which has been formulated with an ionic and anionic surfactant, bicarbonate of soda and slaked lime to form a two phase product. The clear non-emulsified phase is used as a detergent or deodorant. Other emulsifiers have been used with d-Limonene such as polyglycerol oleate, sorbitan esters, or stearates. Typically the system HLB is 3.0 to 8.5. These products have been proven to be ineffective for use with terpenes and similar structured citrus derivatives such as d-Limonene. The attempted emulsions separate rapidly and lead to the possibility of can corrosion at the phase interface. Moreover, in such systems the amount of d-Limonene which can be emulsified is about 45% which results in a rather weak citrus odor.

Diluent or carrier solvents have been proposed to stabilize such systems. In these cases this is an addition of an artificial substance which can be a flammable or toxicological hazard or requires the addition of a strong chemical agent in order to obtain an effective product. The addition of further chemicals have been proposed to reduce the flammability problem. Thus, it has been proposed in the prior art that the problem of flammability encountered with an alcohol or flammable propellant can be reduced by adding methylene chloride or trichloroethane to the composition. See for example, U.S. Pat. No. 4,134,968. However, the art still demonstrates a need for a non-flammable effective d-Limonene room deodorizer which does not contain unnecessarily hazardous propellants or solvents and maximize the amount of d-Limonene in the aerosol spray.

SUMMARY OF THE INVENTION

The present invention is directed to an improved aerosol citrus oil containing space deodorizer and a process for making same. More particularly the invention relates to a non-flammable terpene, preferably d-Limonene containing room deodorizer which contains a polyethylene glycol nonylphenol ether emulsifier.

Emulsions generally are classified as being either of the water-in-oil type or of the oil-in-water type. In a water-in-oil emulsion, the water is present in the form of small droplets dispersed in a continuous oil phase. In an oil-in-water emulsion, the oil is present in the form of small droplets dispersed in a continuous water phase. According to the invention a water-in-oil emulsion is provided which after placing in an aerosol can, filling with propellant preferably an alkane propellant and holding for 12 to 24 hours at room temperature converts to a stable oil-in-water emulsion.

According to the invention, a deodorizing terpene preferably a citrus oil distillate containing substantial amounts of d-Limonene is emulsified with polyethylene glycol nonylphenyl ether to form an oil phase. The resulting oil phase is added to a water phase having a pH of from 8.5 to 10 to form a water-in-oil emulsion having a viscosity under 500 cps preferably about 100 cps. The resulting emulsion is then used as the deodorizing concentrate for filling the aerosol cans. A propellant, preferably an alkane propellant is then added to the cans in an amount of 25-40% of the concentrate. The product is then held for 12 to 24 hours at room temperature during which time it forms a non-flammable, stable oil-in-water, emulsion which can be used as a highly effective aerosol space or room deodorant.

The preferred embodiment of the present invention is illustrated in the drawings and examples. However, it should be expressly understood that the present invention should not be limited solely to the illustrative embodiment.

DETAILED DESCRIPTION OF THE INVENTION

According to the invention a non-flammable citrus oil distillate containing room deodorizer and a method of manufacture is provided. The product emulsion begins as a water-in-oil emulsion and converts to a stable oil-in-water emulsion after it is charged into the aerosol can and a propellant preferably an alkane propellant is added. The resulting product is non-flammable despite the use of the flammable alkane propellant and the use of a high concentration of citrus oil distillate.

According to the invention a deodorizing terpene preferably d-Limonene is emulsified with an organic emulsifier such as polyethylene glycol nonylphenyl ether and petroleum sulfonic acid emulsifiers or the sodium salts thereof to form an oil phase. The oil phase is then mixed with water to form a low viscosity water-in-oil emulsion which is used as a concentrate to fill the aerosol cans. A propellant is then added. The filled cans are then held at room temperature for 12 to 24 hours. The resulting product is a stable non-flammable oil-in-water emulsion.

According to the invention a concentrate for use in manufacturing an aerosol room deodorant is formed by mixing a citrus oil distillate containing substantial amounts of d-Limonene preferably in an amount of 60 to 70 parts by weight of the resulting concentrate composition with 1.0 to 3.5 parts by weight (preferably 1.2 to 2.5) of an organic emulsifier composed of polyethylene glycol nonylphenyl ether and/or a petroleum sulfonic acid emulsifier (preferably a mixture of both) to form an oil phase. The oil phase is then added to a water phase containing 20 to 30 parts by weight of water having a pH of 8.5 to 10 under vigorous mixing to form a low viscosity water in oil phase which is the concentrate for filling the aerosol container. The resulting concentrate has a viscosity under 500 cps preferably about 100 and is easily pumpable and thus can be easily charged into the aerosol cans.

Preferably the water phase is prepared in a vat by charging 20 to 30 parts by weight of deionized water into the vat. The water pH is then adjusted to between 8.5 and 10 with NaOH. Preferably preservatives to retard microbial growth are added. For example, preferably sodium nitrite is added in an amount of about 0.2 parts by weight and sodium benzoate in an amount of 0.1 parts by weight.

The concentrate is then pumped to a concentrate filler and used to fill an aerosol can. A propellant preferably an alkane propellant, most preferably isobutane, propane or butane or a blend thereof is added to the aerosol can in an amount of 25 to 40% by weight of the water in oil concentrate contained in the aerosol can at the propellant filler. The propellant filled can is then maintained at room temperature for from 12 to 24 hours prior to use. The resulting composition upon standing forms a stable single phase oil-in-water emulsion which has a high viscosity and a high percentage of d-Limonene. The resulting aerosol product is a stable, single phase, non-flammable product which has a highly effective deodorizing effect.

The dispensing valve for the resulting spray room deodorant is preferably a system that has a miniature homogenizer chamber with a vapor tap for example, the Aquasol System of Precision Valve Corp. of Yonkers, N.Y.

Other emulsion systems have been tried which use glyceryl oleates and sorbitan esters as the emulsifiers. The resulting d-Limonene product is flammable, at citrus oil concentrations such as used here which provide effective room deodorizers. Such prior systems can separate into phases in the can. It should be noted that the deodorizing composition of the present invention is non-flammable despite the fact that the citrus oil component is itself flammable as is the alkane propellant.

EXAMPLE 1

A non-flammable, stable aerosol deodorizing composition according to the invention was prepared as follows:

1100 lb of a citrus oil extract containing d-Limonene was mixed with 24.27 lb of SOLE MULSE B emulsifier, a product of Hodag Corp. Skokie, Ill. in a vat to form an oil phase. SOLE MULSE B is a mixture of polyethylene glycol nonylphenyl ether Ch. Abs. Serv. (CAS) No. 9016-45-9 and petroleum sulfonic acid CAS No. 68608-26-4. In a separate vat a water phase was prepared. 488 lb (58 gallons) of deionized water was charged into the vat under vigorous mixing, 3.24 lb of sodium nitrite and 1.62 lb of sodium benzoate were added to the water. The pH of the water was adjusted to between 8.5 and 10 by adding NaOH. The oil phase prepared above was then added to the water phase through an inlet under vigorous mixing to form a water-in-oil emulsion.

The resulting concentrate was then fed to the concentrate filler where aerosol cans were filled with the concentrate. The concentrate filled cans were then sent to the propellant charger where the cans were filled with a blend of isobutane and propane as propellant in an amount of 35% by weight of the concentrate contained in the can. The valving system used was the Aquasol System of Precision Valve Corp. of Yonkers, N.Y. The cans were then held at room temperature for 24 hours. The resulting aerosol product was a stable, non-flammable, single phase, room deodorant having a highly effective deodorizing effect and having a pleasant citrus smell.

The foregoing is considered as illustrative only to the principles of the invention. Further, since numerous changes and modifications will occur to those skilled in the art, it is not desired to limit the invention to the exact construction and operation shown and described above, and accordingly all suitable modifications and equivalents may be resorted to, falling within the scope of the invention.

I claim:

1. A process for making a non-flammable, aerosol, d-Limonene composition comprising:
   preparing a pumpable aerosol concentrate having a viscosity under 500 cps by:
   forming an oil phase by:
   mixing a citrus oil distillate containing substantial amounts of d-Limonene in an amount of 60 to 70 parts by weight with 1.0 to 3.5 parts by weight of an emulsifier composed of polyethylene glycol nonylphenyl ether or petroleum sulfonic acid;
   forming a water phase by:
   adding 20 to 30 parts by weight of water to a tank;
   adjusting the pH of said water in said tank to between 8.5 and 10;
   adding the oil phase to the water phase under vigorous mixing to form a low viscosity water-in-oil phase concentrate;
   pumping said water-in-oil phase concentrate to a concentrate filler;
   filling an aerosol can with the water-in-oil phase concentrate;
   charging a alkane propellant to concentrate filled aerosol can in an amount of 25 to 40% by weight of the water-in-oil concentrate contained in the aerosol can;
   maintaining the charged aerosol at room temperature for 12 to 24 hours prior to use so that a single phase non-flammable oil-in-water emulsion having high viscosity is found.

2. The process of claim 1 further comprising: adding sodium nitrite or sodium benzoate to said tank when forming said water phase in a sufficient amount to retard bacterial growth;

3. The process of claim 2 wherein the sodium nitrite is added an amount of 0.2 parts by weight and the sodium benzoate is added in an amount of 0.1 part by weight.

4. The process of claim 1 wherein said emulsifier is added in an amount of 1.2 to 2.5.

5. The process of claim 1 wherein said emulsifier is polyethylene glycol nonylphenyl ether.

6. The process of claim 4 wherein said emulsifier is polyethylene glycol nonylphenyl ether.

7. The process of claim 4 wherein the emulsifier is a mixture of polyethylene glycol nonylphenyl ether and petroleum sulfonic acid.

8. The process of claim 4 wherein said propellant is an alkane propellant.

9. The process of claim 1 wherein said propellant is butane or propane.

10. The process of claim 8 wherein said alkane propellant is butane or propane.

11. The process of claim 1 wherein said citrus oil distillate is substantially composed of d-Limonene.

12. The process of claim 4 wherein said citrus oil distillate is substantially composed of d-Limonene.

13. The process of claim 11 wherein said emulsifier is polyethylene glycol nonylphenyl ether.

14. An aerosol room deodorant comprising a nonflammable oil-in-water emulsion comprising:
   60 to 70 parts by weight of a citrus oil distillate containing substantial amounts of d-Limonene;
   1 0 to 3.5 parts by weight of an emulsifier selected from the group of polyethylene glycol nonylphenyl ether and petroleum sulfonic acid;
   20 to 30 parts by weight water; and a propellant in an amount of from 25 to 40% by weight of the other component of the aerosol room deodorant.

15. The aerosol room deodorant of claim 14 wherein said emulsifier is present in an amount of 1.2 to 2.5 parts by weight.

16. The aerosol room deodorant of claim 15 wherein said propellant is propane or butane.

* * * * *